United States Patent [19]

Arceci et al.

[11] Patent Number: 5,369,009
[45] Date of Patent: Nov. 29, 1994

[54] ANTIBODIES FOR P-GLYCOPROTEIN ENCODED BY THE MDR1 GENE AND USES THEREOF

[75] Inventors: Robert J. Arceci, Westwood; James M. Croop, Jamaica Plain, both of Mass.

[73] Assignee: Dana Farber Cancer Institute, Boston, Mass.

[21] Appl. No.: 870,627

[22] Filed: Apr. 17, 1992

[51] Int. Cl.5 .................. G01N 33/574; G01N 33/53; C12N 5/12; C07K 15/28
[52] U.S. Cl. .................. 435/7.23; 435/7.21; 435/243; 435/240.27; 424/9; 424/1.49; 530/387.7; 530/388.8
[58] Field of Search .......... 435/7.23, 7.21, 243, 435/240.27; 424/9, 1.1; 530/387.7, 388.8

[56] References Cited

U.S. PATENT DOCUMENTS 4,331,647 5/1982 Goldenberg .................. 424/1

OTHER PUBLICATIONS

Kohler, G., et al. Nature 256:495 (1975).
Huse, et al., Science 246:1275 (1989).
Engvall and Pearlmann, Immunochemistry 8:871 (1971).
Jablonski, Anal. Biochem. 148:199 (1985).
Georges, E., et al. Proc. Natl. Acad. Sci., USA, 87:152–156.
Scheper, et al., Int. J. Cancer, 42:389–394 (1988).
Meyers, et al., Cancer Research, 49:3209–3214 (1989).
*Practice & Theory of Immunoassays*, Tijssen, ed., Elsevier Science Publishers, Amsterdam, The Netherlands, pp. 117–121, 1985.
Hamada, H., et al., PNAS USA, vol. 83, pp. 7785–7789, Oct. 1986.
Areci, R. J., et al., Proc. Annu. Meet. Am. Assoc. Cancer Res., vol. 33, A2815, 1992.
Hill, Handbook of Experimental Pharmacology, vol. 72, pp. 673–697, 1984, Abstract only.
Mizuno, et al., Cancer Chemother. Pharmacol., vol. 26, pp. 333–339, 1990, Abstract only.

*Primary Examiner*—Toni R. Scheiner
*Attorney, Agent, or Firm*—David G. Conlin; Ronald I. Eisenstein

[57] ABSTRACT

A novel antibody capable of binding to a 170,000 dalton P-glycoprotein encoded by the mdr1 gene, wherein said antibody binds to an external epitope on the protein and does not substantially increase the intracellular accumulaton or the cytoxicity of either Daunomycin or vinblastine in multidrug resistant cells is described. Methods of use of such antibodies are also described.

21 Claims, 11 Drawing Sheets

ANTIBODIES FOR P-GLYCOPROTEIN ENCODED BY THE MDR1 GENE AND USES THEREOF

This invention is directed to the detection, quantification and classification of P-glycoprotein encoded by the mdr1 gene in body tissues or body fluids, and isolation of cells expressing P-glycoprotein, more particularly to the detection and quantification of such protein in specific tissues associated with tumors using an antibody specific for an external epitope of such protein, as well as therapy using such antibody.

Resistance of malignant tumors to chemotherapeutic agents remains the major cause of failure in cancer therapy. Some tumors are resistant at the onset of therapy to many of the most active cytotoxic agents. Others which are initially responsive develop resistance to a broad range of agents during the course of therapy. Understanding the intrinsic and acquired resistance of malignant tumors to chemotherapeutic agents remains one of the major challenges in developing successful strategies for the treatment of patients with cancer.

The analysis of cell lines displaying resistance to multiple drugs in vitro has provided significant insight into the mechanisms of multidrug resistance. A multigene family, designated mdr for multidrug resistance, has been identified which encodes a family of membrane glycoproteins, termed P-glycoproteins. The mdr gene is overexpressed in multidrug resistant cell lines which, although selected for resistance to a single cytotoxic agent, display cross-resistance to a broad spectrum of structurally and functionally unrelated compounds. The P-glycoprotein appears to function as an energy dependent transport pump capable of effluxing a variety of cytotoxic agents and thus decreasing their intracellular concentration. The primary amino acid structure of the P-glycoprotein indicates that it is related to a large superfamily of evolutionarily and functionally diverse proteins which contain a highly conserved functional unit involved in transporting a variety of substrates across the plasma membrane.

The compounds which comprise the multidrug resistance phenotype include many of the most potent natural product agents currently used in cancer chemotherapy —the antracyclines, Vinca alkaloids, epidophyllotoxins and certain protein synthesis inhibitors such as actinomycin D. There is decreased accumulation and increased efflux of these cytotoxic agents from the multidrug resistant cell lines. In addition, a variety of compounds have been identified which are capable of reversing the multidrug resistant phenotype in drug resistant cells. These agents, which include verapamil, quinidine, progesterone, tamoxfen and Cyclosporin A, are capable of dually interacting with the P-glycoprotein and inhibiting its drug efflux function. Clinical trials with several of these compounds have recently been initiated to evaluate their effect in patients with resistant tumors.

Thus, the potential value of understanding the functional role of the mdr gene family relates not only to extending our knowledge of the basic biological processes involved in membrane transport, but may also provide real therapeutic options for patients in the treatment of cancer.

The mammalian mdr multigene family is differentially expressed in both normal and malignant tissues. The highest levels of expression are found in the adrenal gland and a variety of specialized secretory epithelial surfaces, including the proximal tubule of the kidney, the billiary epithelium in the liver, the intestinal and colonic epithelium and the secretory epithelium of the murine uterus under the control of estrogen and progesterone, suggesting that specific transport functions are associated with each of the genes. Expression of the P-glycoprotein is also observed in the capillary endothelium of blood vessels in the brain and testes.

It would be desirable to have a method for quantitatively measuring the amount of the P-glycoprotein expressed in vivo.

It would also be desirable to have a method of measuring this protein which does not effect or has a minimal effect on the functional aspects of P-glycoprotein.

SUMMARY OF THE INVENTION

We have now generated, isolated and characterized an antibody, preferably a monoclonal antibody, which will specifically bind to an external epitope of a 170,000 dalton P-glycoprotein encoded by the human mdr1 gene and can be used in detecting P-glycoprotein in bodily fluids or tissues, which comprise reacting a fluid or tissue sample with the antibody, or an immunoreactive fragment thereof, wherein the antibody binds to an external epitope of the P-glycoprotein and the antibody does not increase the intracellular accumulation or the cytotoxicity of either daunomycin or vinblastine in multidrug-resistant cells. Immunoblot and immunoassays using the antibody or fragments described above are also disclosed. The bodily fluids or tissues samples can be removed from the patient or one can inject a labelled antibody into a patient and then scan for accumulation of the labelled antibody.

The BRIEF DESCRIPTION OF THE FIGURES

FIG. 1A, 1B, 1C, 1D, 1E, and 1F represent flow cytometric analysis using a preferred antibody in different cell lines. FIG. 1A, CEM (drug sensitive cell line; Fig 1B, CEM/VBLO.3 (CEM/VBL 250) FIG. 1C, CEM/VBL. 5 (CEM/VBL 500); FIG. 1D, BRO (drug sensitive cell line); FIG. 1E, mdr1 transfected cell line; FIG. 1F, mdr3 transfected cell line. Solid line shows staining with MAB 4E3. Dashed line shows staining with IgG2a isotype control.

FIGS. 2A and 2B are a comparison of immunoprecipitation of P-glycoprotein with 2 monoclonal antibodies 4E3 and C219. Lanes 1—represent precipitation of CEM while lanes 4—6 show precipitations of CEM/VBLO.3. Lanes 1,4) IgG2a. Lanes 2,5) C219. Lanes 3,6) 4E3. FIG. 2A shows results in CHAPS buffer (mild denaturation) while FIG. 2B shows results in SDS/Triton ×100 buffer (Stringent denaturation).

FIG. 3A is an autoradiograph of $^{35}$S-methionine labeled 70 kd protein immunoprecipitated by a preferred antibody. Lanes 1,2) CEM with 4E3 and IgG2a respectively; Lanes 3,4) CEM/VBLO.3 with 4E3 and IgG2a respectively.

Figure 5A:
Figure 5B:
Figure 5C:
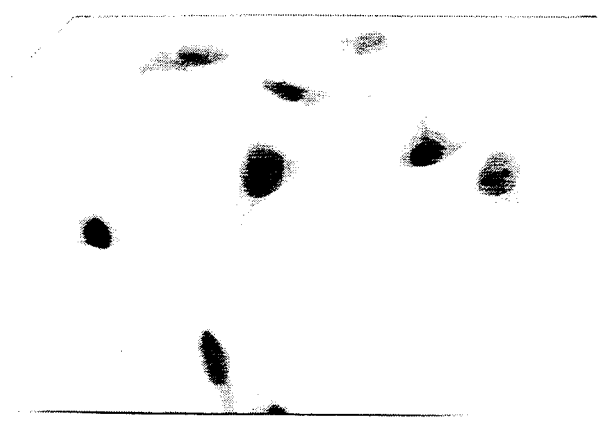
Figure 5D:
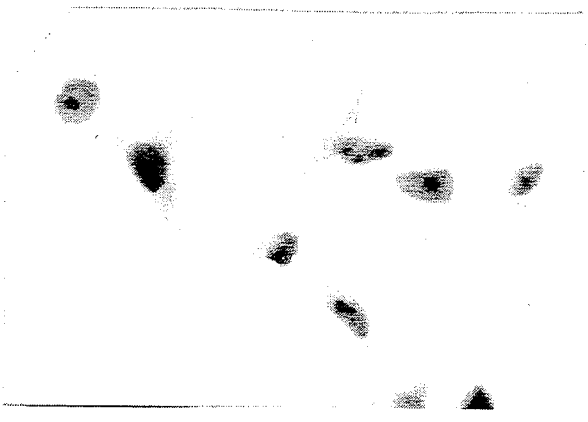
Figure 5E:
Figure 5F:
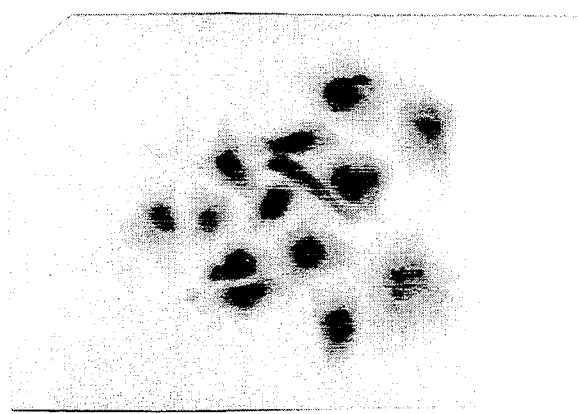
Figure 5G:
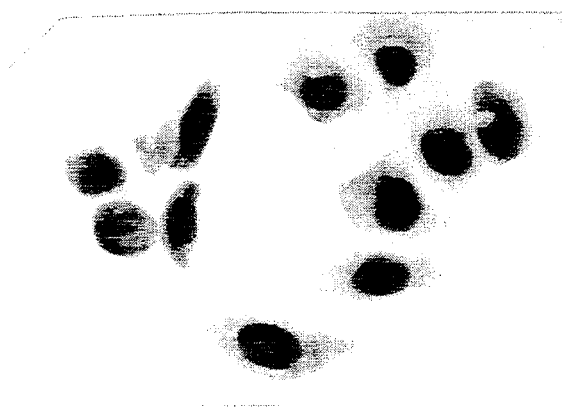
Figure 5H:
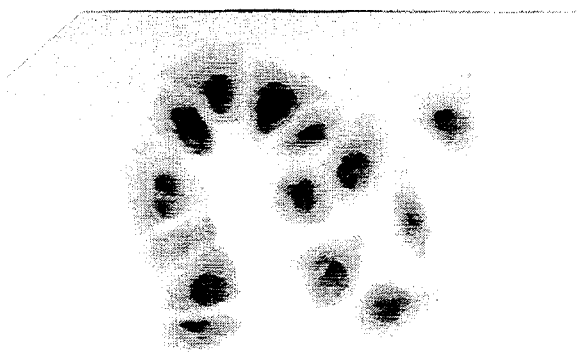

FIGS. 5A, 5B, 5C, 5D, 5E, 5G, and 5H show Immunohistochemical staining on cell lines expressing differing amounts of P-glycoprotein. FIG. 5A, SW1573/500 with 4E3; FIG. 5B, SW1573/500 with IgG2a; FIG. 5C, SW1573 with 4E3, FIG. 5D, SW1573 with IgG2a; FIG. 5E, Alexander Aria/0.5 with 4E3; FIG. 5F, Alexander Aria/0.5 with IgG2a; FIG. 5G, Alexander with 4E3; FIG. 5H, Alexander with IgG2a.

Figure 6A:
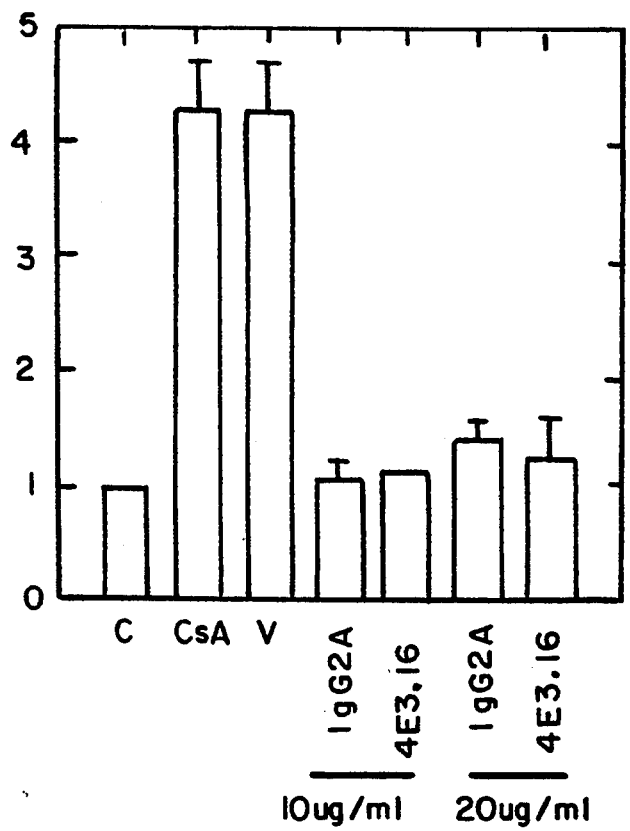
Figure 6B:
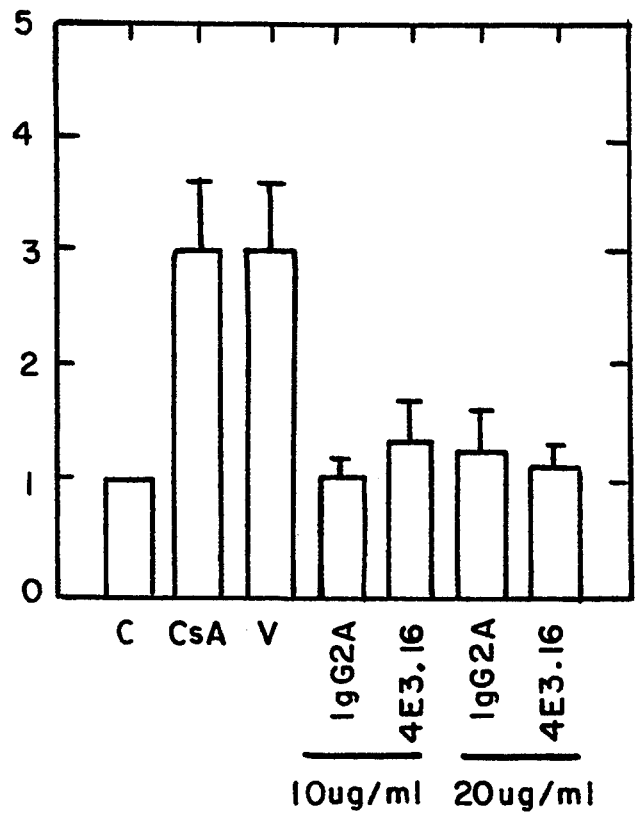

FIGS. 6A and 6B show the intracellular accumulation of $^3$H-Daunomycin (FIG. 6A) and $^3$H-vinblastine (FIG. 6B) in multidrug resistant cells in the presence of different concentrations of MAB 4E3.

Figure 7:
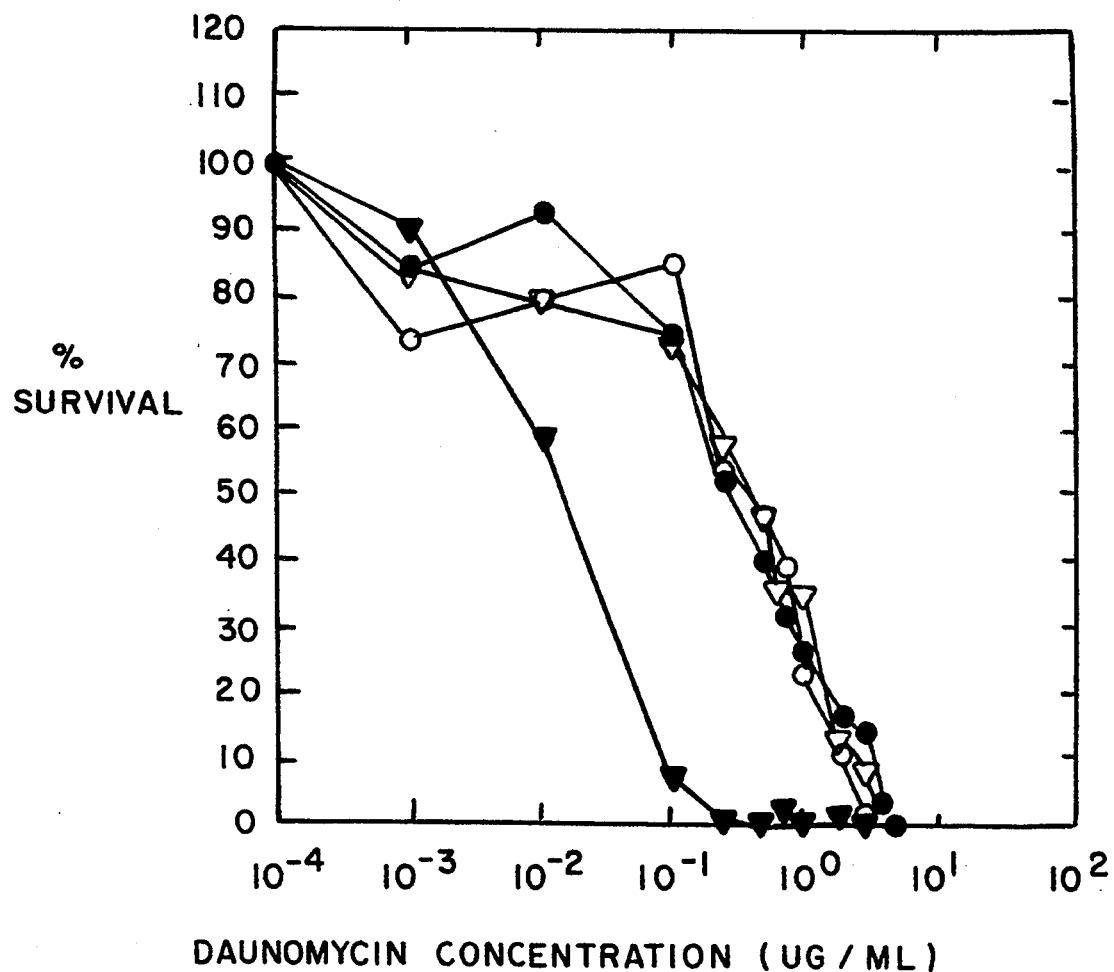
Figure 8A:
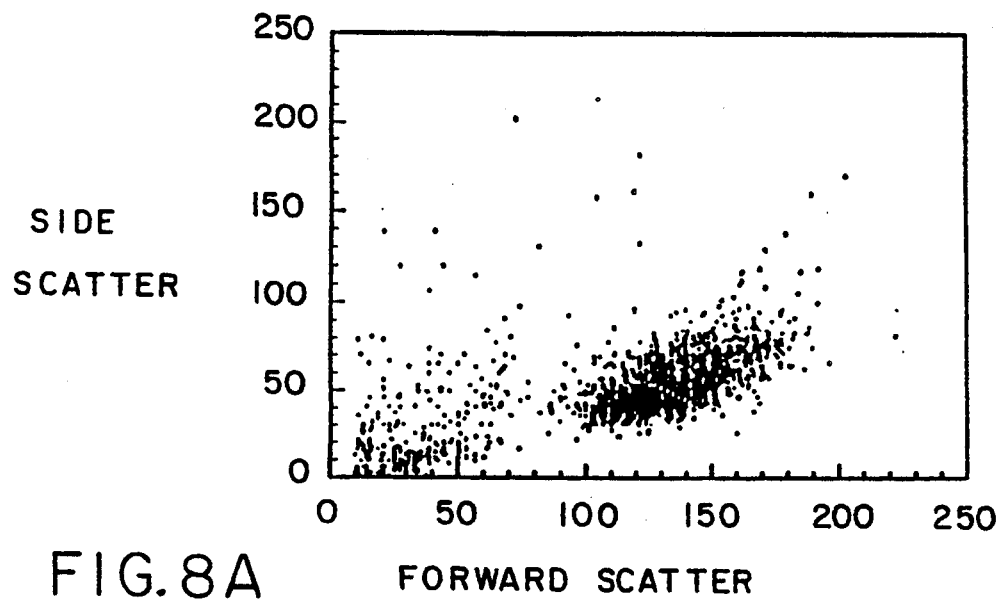
Figure 8B:
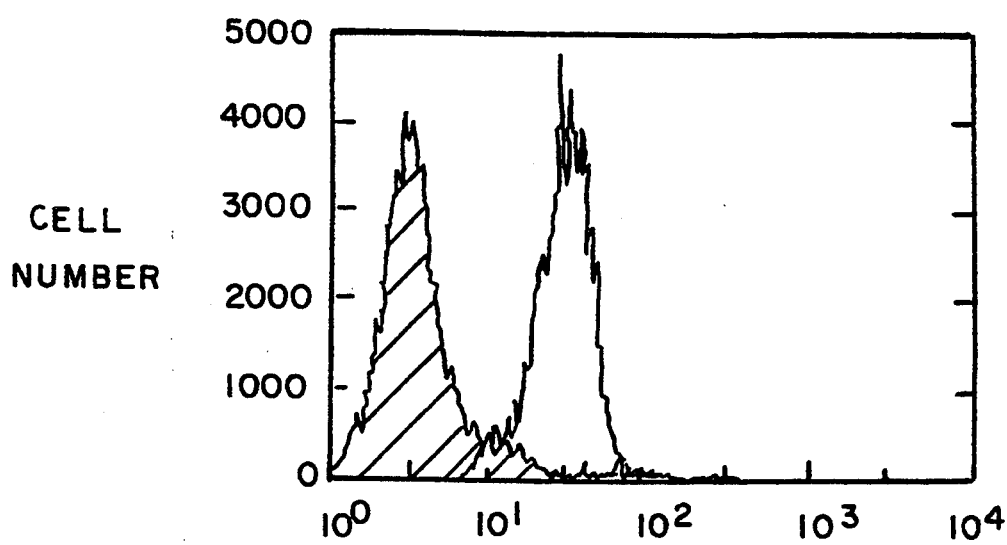
Figure 8C:
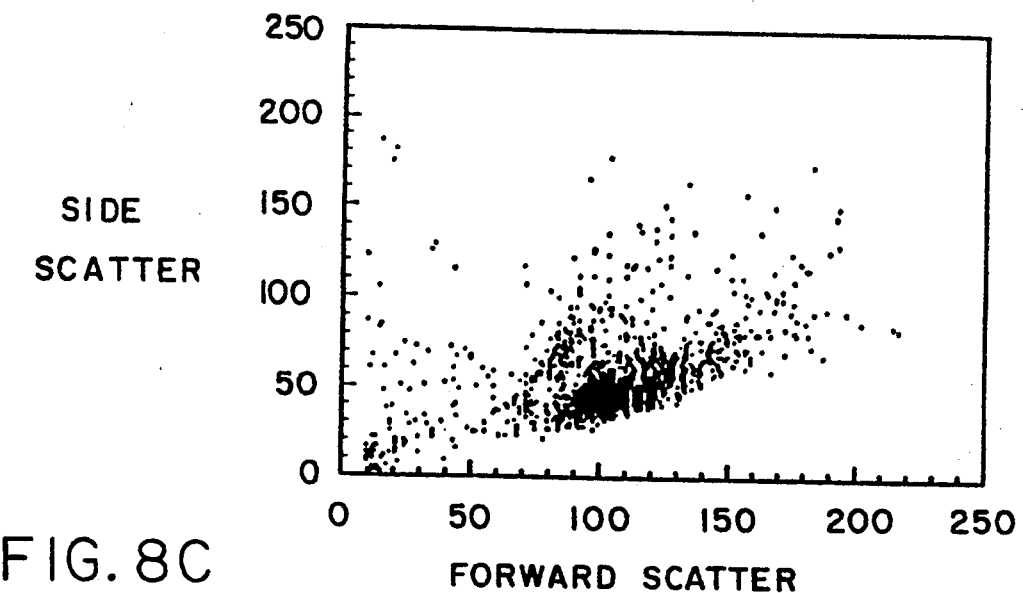
Figure 8D:
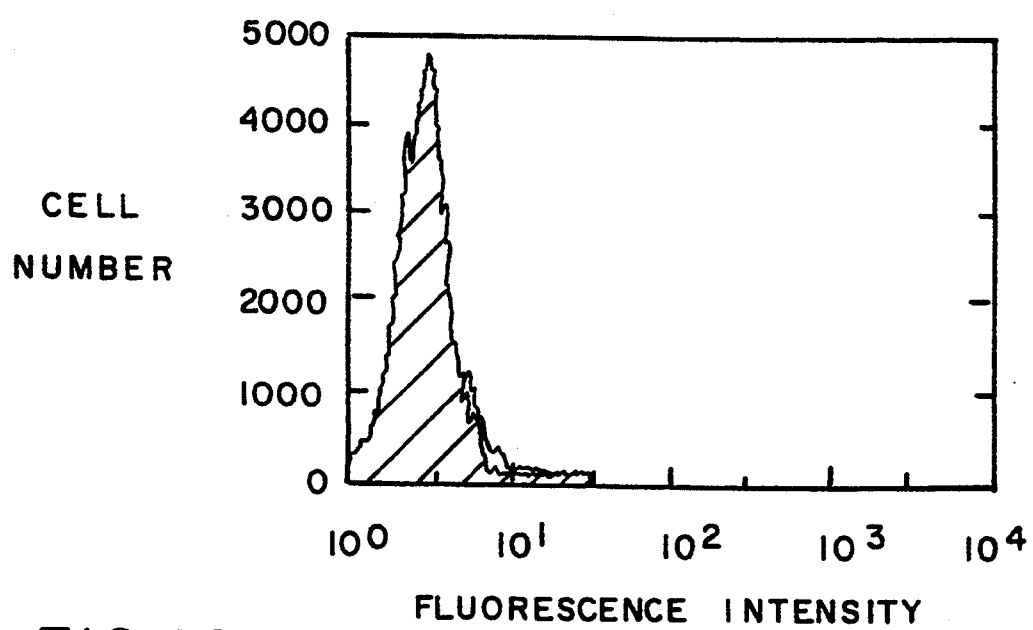

FIG. 7 shows the effect of MAB 4E3 on cell growth in the presence of increasing concentrations of Daunomycin.

FIGS. 8A, 8B, 8C, and 8D show flow cytometric analysis with 4E3 of human acute myelogenous leukemia specimens expressing P-glycoproteins (upper) and not expressing P-glycoprotein (lower).

Figure 9A:
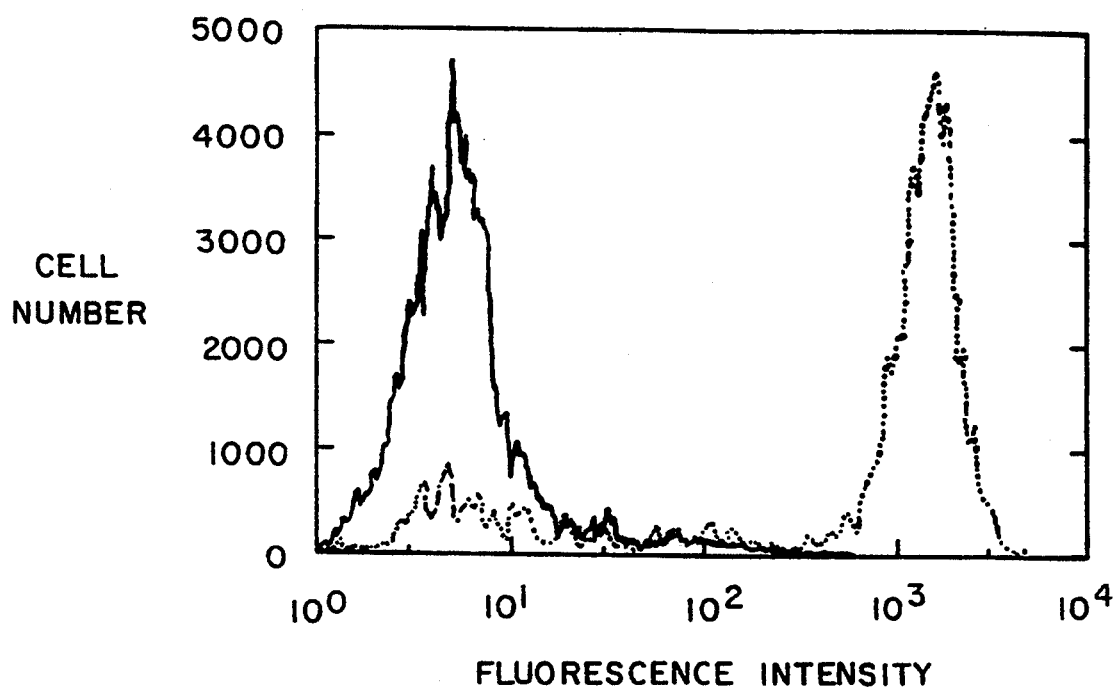
Figure 9B:
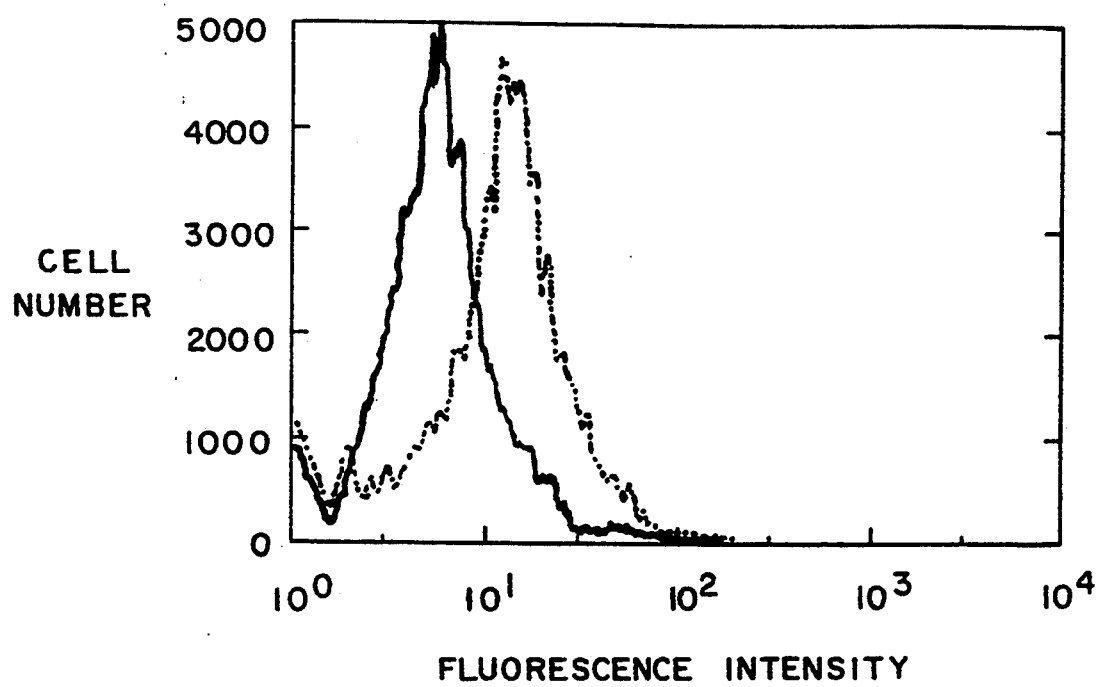

FIGS. 9A and 9B show staining flow cytometric analysis with 4E3 of normal human bone marrow cells following recovery from chemotherapy.

DETAILED DESCRIPTION OF THE INVENTION

The antibodies described herein will bind to an external epitope of a 170,000 dalton human mdr1 gene encoded P-glycoprotein. The antibody will bind to the protein in its native configuration and under relatively mild denaturation conditions, but not under more stringent denaturation conditions, i.e., in the presence of SDS. The antibody will also recognize the non-glycosylated form as well as the glycosylated form of P-glycoprotein.

The presently described antibodies can be either monoclonal or polyclonal antibodies, although monoclonal antibodies are preferred. Furthermore, as used herein, the term antibody includes whole immunoglobulin as well as antigenic binding fragments (i.e. immunoreactive fragments) thereof, which display the above characteristics. The antibody is preferably generated to native P-glycoprotein, although one can prepare an immunogenic peptide that has the basic conformational structure of P-glycoprotein and use that to generate the peptide. Such peptides can be synthesized by conventional means. The antibodies can be prepared by techniques well known to the skilled artisan. For example, the protein or an antigenic portion thereof can be conjugated to keyhole limpet hemocyanin (KLH) and used to raise an antibody in an animal such as a rabbit. Typically the peptide-KLH conjugate is injected several times over a period of about two months to generate antibodies. Antibodies are collected from serum by standard techniques and screened to find an antibody specific for the external epitope of P-glycoprotein. Monoclonal antibodies can be produced in cells which produce antibodies and used to generate monoclonal antibodies by using standard fusion techniques for forming hybridoma cells [Kohler, G., et al. Nature 256:495 (1975)]. Typically this involves fusing an antibody producing cell with an immortal cell line such as a myeloma cell to produce the hybrid cell. Alternatively, monoclonal antibodies can be produced from cells by the method of Huse, et al., Science 246:1275 (1989), both Kohler and Huse are incorporated herein by reference.

For example, hybridomas can be generated by immunization of mice with viable cells expressing the P-glycoprotein. Preferably, these cells express the full length protein, although partial domains can also be used. Using the full length protein as an immunogen, it is possible to generate a collection of monoclonal antibodies with specificities that span the entire length of the protein. This is as opposed to the use of peptide immunogens or short polypeptides generated by prokyryotic systems, which present a more limited number of epitopes from the original protein and hence raise an immune response of more limited specificity. Furthermore, the protein should not be fully denatured.

The mice, for example, SJL mice, can be immunized intraperitoneally (I.P.) with a sufficient number of viable cells of the host cell, which expresses essentially no P-glycoprotein. Cyclophosphamide injection intraperitonially can be done one and two days following the primary injection. About two weeks following immunization, mice are then injected with a sufficient amount of multidrug resistant cells expressing high levels of P-glycoprotein and then allowed another two weeks at which time the entire procedure is repeated. Alternatively, with for example SJL mice, there can be 12 I.P. injections of different types of cells, which, however, express the P-glycoprotein, every 1-2 weeks. This would be followed with a single large injection of P-glycoprotein expressing cell. Four days following the last injection of the transformed cells, the animals are sacrificed and their spleens obtained for the first fusion.

Hybridomas are produced by fusing cells by standard techniques, such as from immunized mice with SP2/O myeloma cells by a polyethylene glycol (PEG) method. Cells are aseptically removed from immunized mice and a single cell suspension of the spleen cells obtained by perfusing the spleen with serum-free media (e.g., DMEM). Spleen cells and myeloma cells are mixed together at a ratio, for example, of 5 to 1, spleen cells to myeloma cells. The cells are then centrifuged and the supernatant removed by aspiration. The cells are then grown in medium by standard techniques. Hybridomas, which grow after the fusion procedure, are then screened for secretion of antibodies which show high levels of binding to MDR cells and not the drug sensitive parental cells. Screening can be done on fixed cells or cell lysates or by cell surface immunofluorescence staining of live cells. Hybridomas that produce positive results are expanded and cloned by limiting dilution to assure that the cells and resulting antibodies are indeed monoclonal. Hybridoma colonies that test positive for these characteristics and presumably the presence of antibody to mdr-encoded P-glycoprotein are diluted in media to a concentration of, for example, 0.5 hybridoma cells per milliliter. Once colonies grow, the supernatants are again tested for the presence of antibody to the P-glycoprotein. If the results are positive when tested by an ELISA assay, the colonies are cloned again by limiting dilution.

One preferred monoclonal antibody is MAB 4E3, which is an IgG2a mouse monoclonal antibody directed to an external epitope of the human mdr1 encoded P-glycoprotein. A hybridoma expressing this monoclonal antibody has been deposited with the American Type Culture Collection (ATCC), 12301 Parklawn Drive, Rockville, Md. 20852 and given Accession No. HB 11018 on Apr. 15, 1992.

This monoclonal antibody is effective at quantitatively detecting mdr1 encoded P-glycoprotein expression by flow cytometry and by immunocytochemistry. Immunoprecipitation of the P-glycoprotein by this antibody is most effective under moderately denaturing conditions. This monoclonal antibody will also recognize both the glycosylated and non-glycosylated forms. However, the monoclonal antibody does not bind to this P-glycoprotein when it is completely denatured, as determined by immunoprecipitation and Western blot analysis.

Furthermore, this monoclonal antibody does not substantially increase the intracellular accumulation or the cytotoxicity of either daunomycin or vinblastine in multidrug-resistant cells. As used herein substantial increase means that when a multidrug resistant cell, to which 10 to 100 μg/ml of this antibody is added per cell is exposed to 0.001 to 10 μg/ml of daunomycin or amounts of 0.1 to 10 μg/ml vinblastine, the amount of accumulation of the compounds in the cell is no more than 15%, preferably 10% and still more preferably about 5% greater than in a control where no antibody is added, and/or there is no more than about 15% preferably about 10% and still more preferably about 5% more cell deaths, than in a control where no antibody is added. This antibody preferaby also does not substantially increase the cytoxicity of Actinomycin under the same conditions as described above.

It is preferred that the antibodies of the present invention have no effect or at most a minimal effect on P-glycoprotein so that they can be used to detect and screen for cells expressing P-glycoprotein without effecting the functional aspects of the efflux pump or inhibiting the growth of P-glycoprotein cells. This is particularly useful when one uses these antibodies for in vivo screening and isolation of cells. These features distinguish the antibody of the present invention from other monoclonal antibodies which have been previously described. For example, although MRK16 and MRK17 are monoclonal antibodies which have been stated to recognize external epitopes of the P-glycoprotein, they are reported to functionally affect P-glycoprotein. MRK16, an IgG2a isotype, has been reported to modulate intracellular vinca alkaloid and Actinomycin D accumulation as well as cytotoxicity in mdr cells. While MRK17, an IgG1 isotype, was reported to inhibit the growth of mdr cells, although it was reported to have no effect on drug accumulation or to potentiate drug cytotoxicity in mdr cells.

Monoclonal antibodies HYB-612, HYB-241 and HYB-195 have been reported to bind to an external epitope of a 180,000 dalton membrane glycoprotein, but not to the 170,000 dalton P-glycoprotein, which is recognized by C219 and also by the antibodies of the present invention. The HYB antibodies were also stated to increase intracellular vinca alkaloid and Actinomycin D in mdr cells.

Similarly, the antibody C219, although binding to the 170,000 dalton P-glycoprotein, binds to an intracytoplasmic epitope and thus is most effective when the protein is completely denatured, as opposed to the present invention which binds to an external epitope and is thus much more effective for the protein in its native confirmation.

The presence of P-glycoprotein can be determined by assaying for it using the antibodies as a probe. In one preferred embodiment, one would use a quantitative immunoassay procedure. For example, one can determine whether the level of P-glycoprotein has increased or decreased when a treatment has begun. Thus, one can compare results against baseline levels obtained from the materials being sampled. Further, one can take samples from the same individual at various times to monitor continuing levels of expression.

The P-glycoprotein is detectable in body fluids such as blood, serum, plasma, urine, cerebrospinal fluid, supernatant from cell lysate breast aspirates and body tissues.

These antibodies can be used to determine the amount of P-glycoprotein in a sample by contacting the sample, either body fluid or tissue, with at least one of the antibodies, preferably a monoclonal antibody, and determining whether binding has occurred. Preferably, one quantifies the amount of binding that occurs. As aforesaid, immunoreactive fragments of these antibodies can also be used and are included within the definition of antibody as used herein.

The P-glycoprotein is differentially expressed in normal and maliganant tissues. Tumors expressing the highest levels of P-glycoproteins frequently are derived from tissues which express high levels. Thus, one can locate tumors by looking for high levels of binding of the present antibody. Furthermore, it appears that the level of P-glycoprotein expression increases in a tumor after exposure to chemotherapeutic agents as the patient's response to therapy decreases. Thus, by monitoring the level of expression one can determine the most appropriate therapy.

The following tumors are most preferably associated with P-glycoprotein expression-pediatric rhabdomyosarcoma, myeloma neuroblasts, acute myelogenous leukemia, colon carcinoma and adrenoirtical carcinoma.

Additionally, these antibodies can be used to locate, monitor and/or isolate cells in vivo which differentially express P-glycoprotein. For example, the antibody can be labeled with a radionuclide, e.g., 111-indium. The labelled antibody can then be injected intravenously and scanned to determine where the labelled antibody accumulates. Typically, it will differentially accumulate in cells producing high levels of P-glycoprotein. The amount of labeled antibody can readily be determined based upon the present disclosure, and methods for scanning are well known in the art. For example, one can use a scintegraphic camera for scanning. By looking for cells having antibody binding, one can detect cells expressing P-glycoprotein, isolation can be accomplished by standard techniques. Because the described antibody does not substantially increase the intracellular accumulation or the cytoxocity of Daunomycin or Vinblastine in multidrug resistant cells, it permits further analysis without inhibiting the functional transport characteristics of the P-glycoprotein.

In accord herewith, the presently described antibody or a cocktail of probes including antibodies to other proteins that one wishes to monitor at the same time such as a protein produced by and associated with a tumor can be used for detection. The antibody probes can be labeled directly with a reporter or indirectly with a specific binding pair using conventional techniques.

Specific binding pairs can be of the immune or non-immune type. Immune specific binding pairs are exemplified by antigen-antibody systems of hapten/anti-hapten systems. These include fluorescein/anti-fluorescein, dinitrophenyl/anti-dinitrophenyl, biotin/anti-biotin, peptide/anti-peptide and the like.

Non-immune binding pairs include systems wherein the two components share a natural affinity for each other but are not antibodies. Exemplary non-immune pairs are biotin-streptavidin, intrinsic factor-vitamin $B_{12}$, folic acid-folate binding protein and the like.

A variety of methods are available to covalently label antibodies with members of specific binding pairs. Methods are selected based upon the nature of the member of the specific binding pair, the type of linkage desired, and the tolerance of the antibody to various conjugation chemistries. Biotin can be covalently coupled to antibodies by utilizing commercially available active derivatives. Some of these are biotin-N-hydroxy-succinimide which binds to amine groups on proteins; bitoin hydrazide which binds to carbohydrate moieties, aldehydes and carboxyl groups via a carbodiimide coupling; and biotin maleimide and iodoacetyl biotin which bind to sulfhydryl groups. Fluorescein can be coupled to protein amine groups using fluorescein isothiocyanate. Dinitrophenyl groups can be coupled to protein amine groups using 2,4-dinitrobenzene sulfate or 2,4-dinitrofluorobenzene. Other standard methods of conjugation can be employed to couple monoclonal antibodies to a member of a specific binding pair including dialdehyde, carbodiimide coupling, homofunctional crosslinking, and heterobifunctional crosslinking. Carbodiimide coupling is an effective method of coupling carboxyl groups on one substance to amine groups on another. Carbodiimide coupling is facilitated by using the commercially available reagent 1-ethyl-3-(dimethyl-aminopropyl)-carbodiimide (EDAC).

Homobifunctional crosslinkers, including the bifunctional imidoesters and bifunctional N-hydroxy-succinimide esters, are commercially available and are employed for coupling amine groups on one substance to amine groups on another. Heterobifunctional crosslinkers are reagents which possess different functional groups. The most common commercially available heterobifunctional crosslinkers have an amine reactive N-hydroxysuccinimide ester as one functional group, and a sulfdhydryl reactive group as the second functional group. The most common sulfhydryl reactive groups are maleimides, pyridyl disulfides and active halogens. One of the functional groups can be a photoactive aryl nitrene, which upon irradiation reacts with a variety of groups.

The detectably-labelled probe, e.g., antibody, detectably-labelled antibodies, or detectably-labelled member of the specific binding pair is coupled to a reporter which can be a radioactive isotope, enzyme, fluorogenic, chemiluminescent or electrochemical materials. Commonly used radioactive isotopes are $125_I$, $Tc^{99m}$ and $^3H$. Standard radioactive isotopic labeling procedures include the chloramine T, lactoperoxidase and Bolton-Hunter methods for $^{125}I$ and reduction methylation for $^3H$.

Enzymes suitable for use in this invention include, but are not limited to, horseradish peroxidase, alkaline phosphatase, $\beta$-galactosidase, glucose oxidase, luciferase, $\beta$-lactamase, urease and lysozyme. Enzyme labeling is facilitated by using dialdehyde, carbodiimide coupling, homobifunctional crosslinkers and heterobifunctional crosslinkers as described above for coupling an antibody with a member of a specific binding pair.

The labeling method chosen depends on the functional groups available on the enzyme and the material to be labeled, and the tolerance of both to the conjugation conditions. The labeling method used in the present invention can be one of, but not limited to, any conventional methods currently employed including those described by Engvall and Pearlmann, *Immunochemistry* 8: 871 (1971), Avrameas and Ternynck, *Immunochemistry* 8:1175 (1975), Ishikawa et al., *J. Immunoassay* 4 (3):209–327 (1983) and Jablonski, *Anal. Biochem.* 148: 199 (1985), which are incorporated by reference.

Labeling can be accomplished by indirect methods such as using spacers or other members of specific binding pairs. An example of this is the detection of a biotinylated antibody with unlabelled streptavidin and biotinylated enzyme, with streptavidin and biotinylated enzyme being added either sequentially or simultaneously. Thus, according to the present invention, the antibody used to detect can be detectably-labelled directly with a reporter or indirectly with a first member of a specific binding pair. When the antibody is coupled to a first member of a specific binding pair, then detection is effected by reacting the antibody-first member of a specific binding complex with the second member of the binding pair which is labelled or unlabelled as mentioned above.

Moreover, the unlabelled detector antibody can be detected by reacting the unlabelled antibody with a labelled antibody specific for the unlabelled antibody. Such an anti-antibody can be labelled directly or indirectly using any of the approaches discussed above. For example, the anti-antibody can be coupled to biotin which is detected by reacting with the streptavidin-horseradish peroxidase system discussed above.

One preferred embodiment utilizes biotin. The biotinylated antibody is in turn reacted with streptavidin-horseradish peroxidase complex. Orthophenylenediamine, 4-chloro-naphthol, or tetramethylbenzidine (TMB) can be used to effect chromogenic detection.

The preferred immunoassay format for practicing this invention is a forward sandwich assay in which the capture reagent has been immobilized, using conventional techniques, on the surface of the support. Suitable supports used in assays include synthetic polymer supports, such as polypropylene, polystyrene, substituted polystyrene, e.g., aminated or carboxylated polystyrene; polyacrylamides; polyamides; polyvinylchloride, etc.; glass beads; agarose; nitrocellulose, etc.

The present antibody can also be used therapeutically as a carrier for drugs, biologically and chemically produced toxins or cytotoxic agents. These antibodies will differentially locate cells expressing high levels of P-glycoprotein and are an effective method of delivery. The drugs, toxins and cytotoxic materials can be attached to the antibody in the same manner as the other labels resulting in a coupled conjugate. Such coupled antibody conjugates, preferably monoclonal antibody conjugates such as 4E3 conjugates, may also be used to deplete bone marrow or peripheral blood of multidrug resistant cells (i.e., ex vivo depletion) prior to autologous bone marrow transplantation.

The antibody or peptide can be delivered by any of a number of means. For example, either can be administered by parenteral injection (intramuscular (i.m.), intraperitoneal (i.p.), intravenous (i.v.) or subcutaneous (s.c.)), oral or other routes of administration well known in the art. Parenteral administration is preferred.

The amount used will typically be in the range of about 0.1 mg to about 10 mg/kg of body weight. The antibodies and peptides will preferably be formulated in a unit dosage form.

For example, solid dose forms that can be used for oral administration include capsules, tablets, pills, powders and granules. In such solid dose forms, the active ingredient, i.e., antibody or peptide, is mixed with at least one inert carrier such as sucrose, lactose or starch. Such dose forms can also comprise additional substances other than inert diluents, e.g., lubricating agents, such as magnesium stearate. Furthermore, the dose forms in the case of capsules, tablets and pills may also comprise buffering agents. The tablets, capsules and pills can also contain time-release coatings.

For parenteral administration, one typically includes sterile aqueous or non-aqueous solutions, suspensions or emulsions in association with a pharmaceutically acceptable parenteral vehicle. Examples of non-aqueous solvents or vehicles are propylene glycol, polyethylene glycol, vegetable oils such as olive oil and corn oil, gelatin and injectable organic esters, such as ethyl oleate. These dose forms may also contain adjuvants such as preserving, wetting, emulsifying and dispersing agents. They may be sterilized by, for example, filtration through a bacterial-retaining filter, by incorporating sterilizing agents into the composition, by irradiating the compositions, etc., so long as care is taken not to inactivate the antibody. They can also be manufactured in a medium of sterile water or some other sterile injectable medium before use. Further examples of these vehicles include saline, Ringer's solution, dextrose solution and 5% human serum albumin. Liposomes may also be used as carriers. Additives, such as substances that enhance isotonicity and chemical stability, e.g., buffers and preservatives, may also be used.

The preferred range of active ingredient in such vehicles is in concentrations of about 1 mg/ml to about 10 mg/ml. More preferably, about 3 mg/ml to about 10 mg/ml.

The present invention is further illustrated by the following examples. These examples are provided to aid in the understanding of the invention and are not to be construed as a limitation thereof.

Cell Lines

The human T-cell lymphoblastic leukemia cell line, CEM, and its multidrug resistant derivative, CEM/VBL 100 (maintained in 100 ng/ml vinblastine) were kindly provided by Dr. William Beck (St. Judes Hospital for Sick Children, Memphis, Tenn.). The CEM/VBL 250 and CEM/VBL 500 multidrug resistant cell lines, which show increased levels of P-glycoprotein and multidrug resistance compared to CEM/VBL 100, were derived by stepwise selection in increasing amounts of vinblastine of CEM/VBL 100 to a final concentration of 250 ng/ml and 500 ng/ml respectively. ME180/Dox 500 is a multidrug resistant cell line expressing increased amounts of P-glycoprotein and was derived by stepwise selection of the human uterine adenocarcinoma cell line, ME180 (ATCC) in increasing amounts of doxorubicin to a final concentration of 500 ng/ml. Sw-1573/500 and SW-1573 are multidrug resistant and drug sensitive human squamous lung carcinoma cell lines isolated as previously described. The multidrug resistant cell line, Alexander 0.5, is a human hepatoma cell line derived by stepwise selection of the drug sensitive parent in increasing concentrations of doxorubicin to a final concentration of 500 ng/ml. Mdr transfected cell lines, tmdr1 and tmdr3.35 were derived by transfection of the human melanoma cell line, BRO, with full-length mdr1 and mdr3 cDNAs.

Generation of Anti-P-glycoprotein Monoclonal Antibody.

SJL female mice (Jackson Laboratories, Bar Harbor, ME) were immunized with 12 intraperitoneal injections every 1–2 weeks of either 5–10×10$^6$ SW-1573/500 or ME180/Dox 500. Following these injections, a single IV dose of 1×10$^7$ SW-1573/500 cells was given followed three days later by sacrificing the mouse and harvesting the splenocytes. One day prior to the harvesting of the immunized animal, thymocytes and splenocytes were harvested from a 3 to 4 week Balb/c mouse. These thymocytes and splenocytes were mixed in a 1:1 ratio and plated in 96-well plates at a concentration of 2×10$^5$ cells per ml of DMEM medium, supplemented with 20% FCS, HAT (hypoxanthine, azaguanine and thymidine) and 5% 37 1$^O$ Endo" condition medium. The "1$^O$ Endo" conditioned medium is derived from a mouse embryonic cell line which has stimulatory activity for B lymphocyte antibody synthesis (unpublished data). The SJL-derived splenocytes were fused with logarithmically growing P3/NS-1 myeloma cells, which is available from the ATCC, at a 1:3 ratio using PEG (Boeringher-Mannheim), then plated with the "feeders" in the above selection medium. Eleven days later, the supernatants of approximately 3,000 HAT resistant hybridomas were screened by immunofluorescent staining for antibody reactivities which would recognize surface epitopes on live multidrug resistant CEM/VBL 500 and not on the CEM parental cell lines. Approximately 5% of the hybridomas showed reactivity with greater binding to the MDR cell line. Three of these were subsequently repeatedly cloned by limiting dilution. 4E3, an IgG2a isotype, was extensively characterized and is reported on here. The hybridoma expressing this antibody (4E3) was filed with the American Type Culture Collection (ATCC), 12301 Parklawn Drive, Rockville, Md. 20852, pursuant to the Budapest Treaty and given accession number HB 11018.

Flow Cytometry

Tissue cultured cells were collected and washed twice in cold PBS prior to resuspending 1×10$^6$ cells in 100 μl of PBS containing 1:1 dilution of human serum with PBS. The cells were then incubated at 4° C. for 30 minutes to block any Fc receptors. Two ml of PBS were then added to the cells which were collected by centrifugation at 600 xg for 3 minutes. Pelleted cells were resuspended in 100 μl of PBS containing 2% goat serum and 10 μg/ml of 4E3 or a mouse IgG2a isotype matched control antibody. This mixture was incubated for 30 minutes at 4° C. and cells washed twice with cold PBS followed by resuspension in 100 μl of PBS containing 2% goat serum and FITC-labelled goat anti-mouse Ig (Fab)$_2$ fragment (TAGO) at a 1:30 dilution. Cells were incubated with the second antibody for 30 minutes at 4° C. in the dark, followed by two washes in cold PBS and fixation in 2% paraformaldehyde prior to analysis. The level of fluorescence was determined using a Becton-Dickinson FACSCAN II and the LYSYS software application.

Immunohistochemistry

Adherent cell lines were grown on poly-lysine coated Labtech slide chambers or on cover slips to approximately 60% confluency. The slides were then washed in PBS and fixed for 5 minutes at 4° C. in 1% or 4% paraformaldehyde in PBS. The cells were subsequently soaked in 0.05 M Tris-buffered saline pH 7.6) containing 20% horse serum for 30 minutes. Liquid was drained from the slides and the primary or control antibodies at 20 μg/ml in TBS containing 1% goat serum were allowed to bind to the cell surfaces for 1 hour at room temperature in humidified boxes. After washing 3 times in TBS, the slides were incubated with an alkaline phosphatase-conjugated goat anti-mouse secondary antibody (Promega) diluted 1:500 for 1 hour at room temperature. The unbound secondary antibody was wahsed away with TBS and the slides developed using a Fast Red substrate, followed by counterstaining in hematoxylin.

Immunoprecipitation

Immunoprecipitations were done under both mild (CHAPS) and harsh (SDS/Triton X-100) denaturation conditions. Cells were metabolically labelled with $^{35}$S-methionine (Dupont) at 25 to 50 $\mu$Ci/ml overnight or 100 $\mu$Ci/ml for 0.5 to 3 hours at 37° C. in 5% $CO_2$. At the end of the labelling period, cells were collected and washed twice in cold PBS. For immunoprecipitation under mild denaturation conditions, $5 \times 10^6$ cells were lysed in 200 $\mu$l of 50 mM Tris-Cl, pH 8.0, 140 mM NaCl, 2 mM $MgCl_2$, 0.5% CHAPS, 1 mM PMSF, 0.2 U/ml aprotinin, 0.02% sodium azide and 10 mM ATP. After shaking for 30 minutes at 4° C., insoluble material was pelleted by centrifugation at 14,000 xg in a microcentrifuge. The supernatants were transferred to fresh tubes and 50 ul of Protein-G-Sepharose beads (Pharmacia), pre-coated with goat-anti-mouse IgG and albumen, were added and rocked at 4° C. for 1 hour. The beads were then pelleted for 5 seconds in a microfuge and primary antibodies were added at 20 $\mu$g/ml. The supernatants and antibodies were rocked at 4° C. for 2 hours, then 30 $\mu$l of Protein-G-Sepharose beads were added, and the tubes rocked for 1 hour. The beads were then collected by centrifugation and washed 3 times in 50 mM Tris-Cl, pH 8.0, 140 mM NaCl, 2 mM $MgCl_2$, 0.1% CHAPS, 1 mM PMSF, 0.1% bovine hemoglobin and 0.02% sodium azide followed by 3 washes in the same buffer without CHAPS or bovine hemoglobin. The beads were then resuspended in 50 $\mu$l of sample buffer and incubated at room temperature before being pelleted by centrifugation. The supernatants were then electrophoresed on a 7.5% to 15% gradient polyacrylamide gel. Immunoprecipitation under harsher denaturing conditions with SDS/Triton X-100 was performed essentially as described.

Western Blot Analysis

Immunoprecipitated complexes of metabolically-labelled proteins from MDR and parental cell lines were electrophoretically separated as described above and then transferred to nitrocellulose prior to blotting with either the anti-P-glycoprotein monoclonal antibody, C219 (Centocor) or mouse IgG2a isotype control antibody. Western blotting was accomplished using the alkaline phosphatase system detection system as described by the manufacturer (Promega).

Cytotoxic Drug Accumulation Studies

Intracellular accumulation of cytotoxic agents was performed using modifications of standard procedures. $^3$H-Daunomycin was purchased from Dupont, $^3$H-Vinblastine from Amersham. Cells were collected, washed three times in PBS and counted. The cells were resuspended at $1 \times 10^6$ cells per ml RPMI medium containing 10% fetal bovine serum (FBS) and 10mM Hepes. Aliquots of 0.25 ml were dispensed to 75 mm round bottom plastic tubes and MDR reversal agents (cyclosporin A) or antibodies were added. The tubes were incubated in a 37° C. shaking water bath for 30 minutes. At that time, the tritiated cytotoxic agent was added. $^3$H-Daunomycin (Dupont, specific activity 1-5 Ci/mmol) was added as a 1:25 dilution of radiolabelled to unlabelled Daunomycin (250 $\mu$g/ml) such that the final concentration of Daunomycin was 10 $\mu$M. $^3$H-Vinblastine (Amersham, specific activity 5-25 Ci/mmol) was added at a 1:100 dilution of a radiolabelled to unlabelled vinblastine (250 $\mu$g/ml). Following the addition of radiolabelled drug, the tubes were incubated at 37° C. in a shaking water bath for either 1, 2 or 6 hours. At the end of this incubation, the entire contents of each tube were overlayed on a 200 $\mu$l cushion of Dow 550 silicone oil (Dow Corning) and mineral oil at a 4:1 ratio in 1:5 ml Eppendorf tubes. The tubes were centrifuged at 10,000 xg at 4° C. for 1 minute to separate the cells from drug-containing medium. The medium and oil mixture were removed by aspiration and the cell pellets solubilized in 1 ml of 1M NaOH at 60° C. overnight. Glacial acetic acid (0.2 ml) was added to each tube and the contents thoroughly mixed prior to transfer into 10 ml of Biofluor Scintillation Cocktail (Dupont). The radioactivity was quantitated in a Beckman Scintillation Counter with error value of less than or equal to 5%. The "fold increase" in radiolabelled drug accumulation was calculated by dividing the amount of radioactivity in the control tube (i.e., the solvent or control antibody containing tube) into the amount of radioactivity in the tubes containing different concentrations of MDR inhibitors or antibodies. Values reported are the average of at least three experiments with each experiment being done in duplicate.

Growth Inhibition Studies

The inhibition of cell growth was determined using the MTT dye assay. Cells were plated in 96-well plates in RPMI containing 10% FBS and incubated at 37° C. for approximately 1 hour. MDR inhibitors or antibodies at varying concentrations of cytotoxic agents (Daunomycin, vinblastine or actinomycin D) were diluted into the medium and added to the cell suspension (final volume 200 $\mu$l). The cells were incubated for 4 days at 37° C. in 5% $CO_2$ after which time 50 $\mu$l of 2 mg/ml MTT dye (Sigma) in PBS was added to the wells. The plates were incubated for 4 hours at 37° C. and then centrifuged at 450 xg for 5 minutes. The supernatant (225 $\mu$l) was carefully aspirated and 150 $\mu$l of DMSO was added and mixed on a plate shaker for 10 minutes. The optical density of the color reaction in each well was determined by absorbance spectroscopy at 550 nm and 490 nm using a Whittaker EIA Model MA 310 plate recorder with control, negative wells serving as a baseline value.

Preparation of Bone Marrow Specimens

Bone marrow specimens were obtained during diagnostic bone marrow aspiration from patients at the Dana Farber Cancer Institute and Children's Hospital, Boston. Procurement of specimens was reviewed and approved by the Institutional Clinical Investigation Committees. Aspirated bone marrow was diluted in RPMI containing 10% FBS and then underlayered with Lymphocyte Separation Medium (LSM, Organon) followed by centrifugation for 20 minutes at 4° C. at 800 xg. The viable, mononuclear cell population was removed from the medium/LSM interface and washed three times in cold PBS in preparation for flow cytometric analysis.

Flow Cytometric Analysis of 4E3 Surface Staining

Figure 1A:
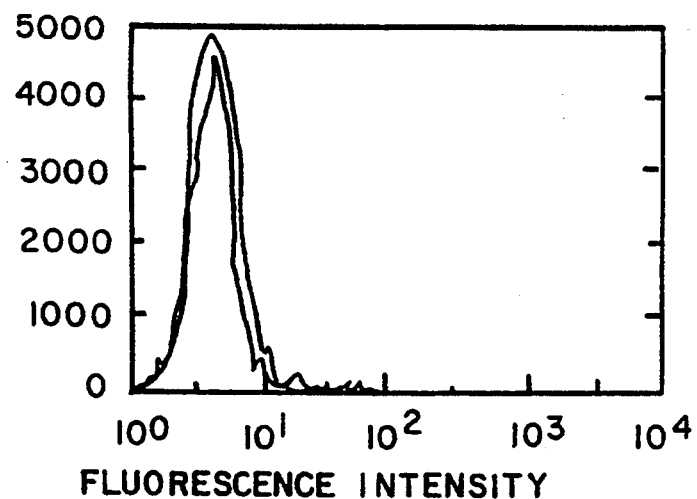
Figure 1B:
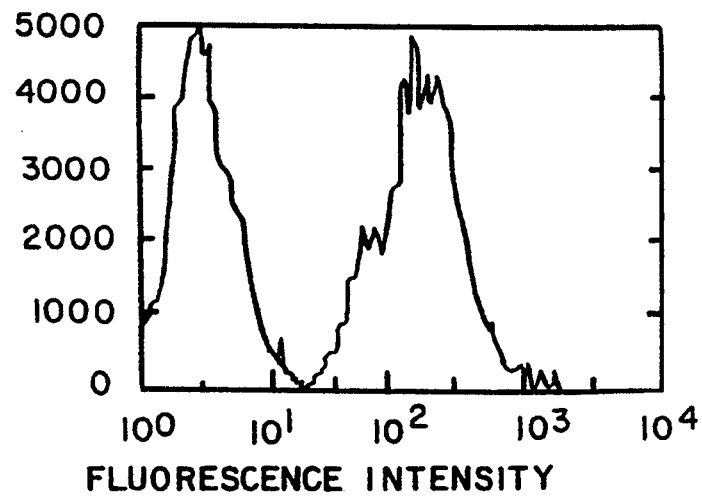
Figure 1C:
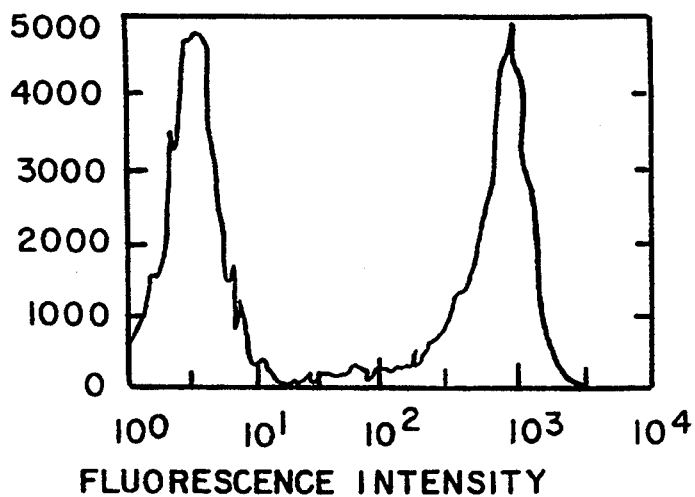

FIG. 1A through 1C demonstrates the surface staining of three human cell lines, none of which were used for immunization, as determined by indirect immunofluorescent staining using 4E3. CEM, a drug sensitive human T-lymphoblastoid derived cell line which does not express P-glycoprotein, shows no detectable surface expression of the 4E3 epitope (FIG. 1A). CEM/VBL 250 and CEM/VBL 500 were both derived by step-wise selection in increasing concentrations of vinblastine of the mdr cell line CEM/VBL 100 resulting in dramatically increased expression of mdr mRNA and increased levels of surface staining with MAB 4E3 (FIGS. 1B and 1C, respectively).

There was no difference in the level of fluorescence between the IgG2a control antibody and the level of detectable surface expression of the 4E3 epitope on the CEM cell line (FIG. 1A). When CEM are first split into fresh medium and in logarithmic growth, a very low amount of immunofluorescent staining was observed with 4E3. As aforesaid, the multidrug resistant derivatives, CEM/VBL 250 and CEM/VBL 500, displayed increased levels of surface staining with the 4E3 monoclonal antibody (See, FIG. 1B and 1C). Immunofluorescent staining with 4E3 on the CEM/VBL 250 cell line shifted the fluorescence intensity by approximately 2.5 logs, while the more highly resistant CEM/VBL 500 shifted the fluorescence intensity approximately 3 logs compared to the IgG2A control antibody.

Figure 1D:
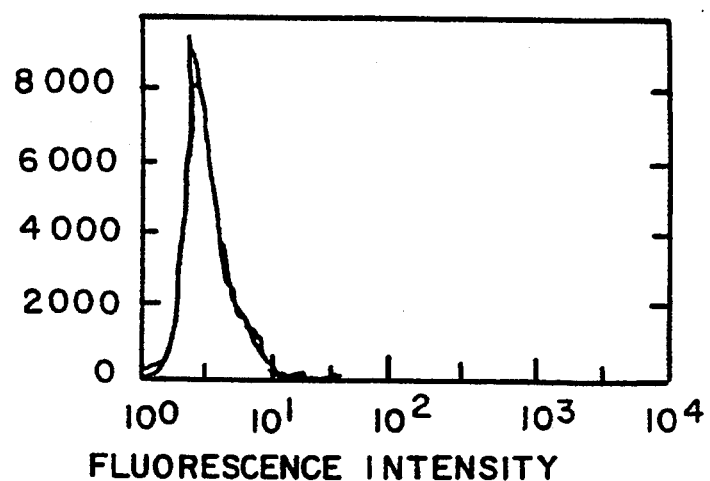
Figure 1E:
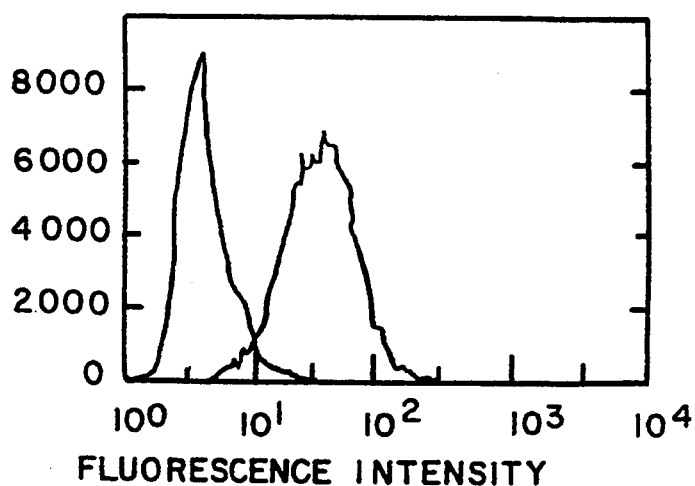
Figure 1F:
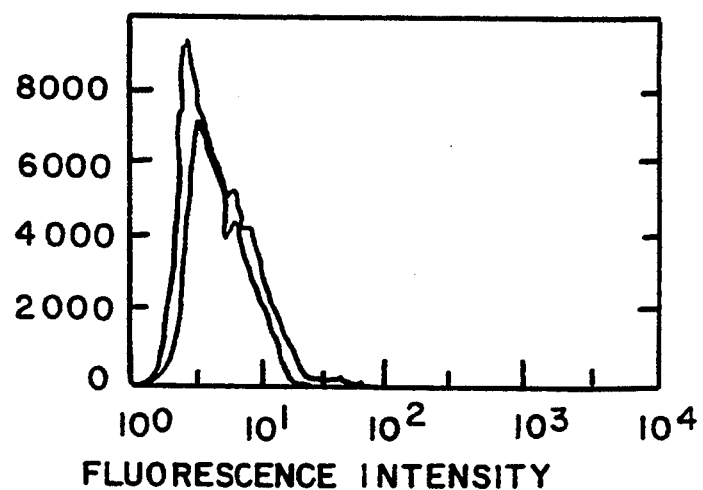

The ability of 4E3 to surface stain mdr1 and mdr3 cDNA transfectants was then tested. MAB 4E3 shows no significant binding to either the parent cell-line, BRO, or to the mdr3 transfected cell line overexpressing mdr3 (FIGS. 1D and 1F, respectively). However, there is significant binding to the mdr1 transfected cell line (FIG. 1E). These results demonstrate that 4E3 shows surface binding to multidrug resistant cells which express the mdr1 gene product but not to mdr3 gene product. No immunofluorescent staining of either hamster or mouse mdr cell lines expressing increased levels of P-glycoprotein showed that 4E3 is specific for the human P-glycoprotein.

Immunoprecipitation of P-glycoprotein with 4E3

Figure 2A:
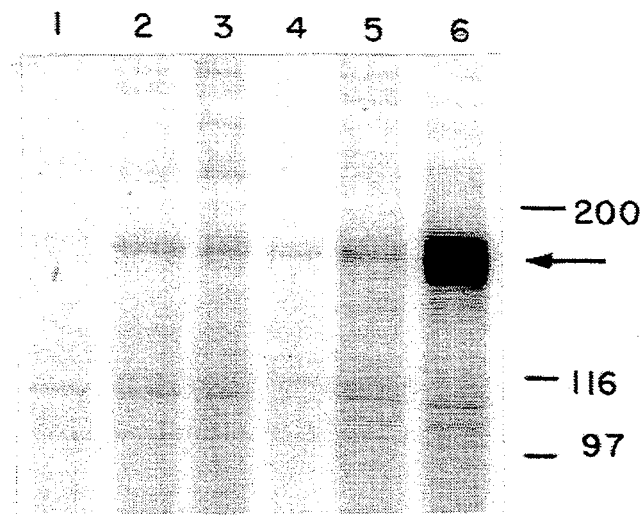
Figure 2B:
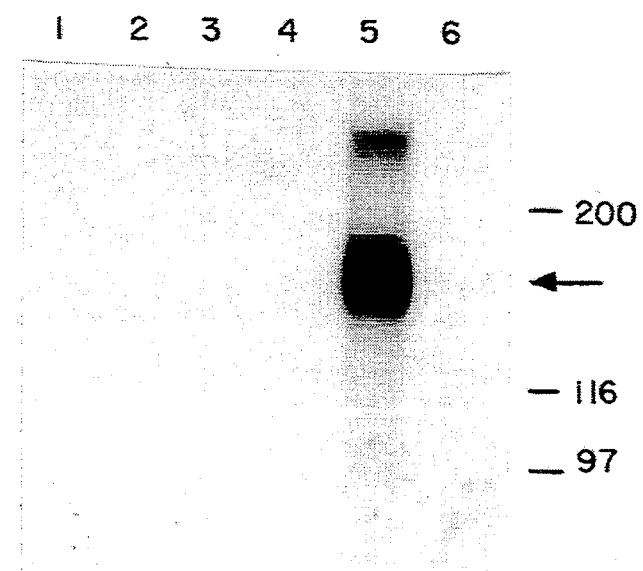

Although the above surface staining studies are consistant with 4E3 recognizing an external domain of the mdr P-glycoprotein, results from immunoprecipitation identify the molecular species which contains the 4E3 epitope. FIG. 2A demonstrates that under relatively mild denaturation conditions, i.e. using 0.5% CHAPS, MAB 4E3 effectively precipitates a 170 kd protein species in the multidrug resistant but not in the drug sensitive parent. Under these immunoprecipitation conditions, the anti-mdr P-glycoprotein MAB C219 does not precipitate very effectively. When immunoprecipitation is done under more stringent denaturation conditions, i.e., in the presence of SDS and Triton X-100, the binding of MAB 4E3 is completely lost, whereas, C219 is quite effective in precipitating the 170 kd P-glycoprotein (FIG. 2B). These results are consistent with the manner in which the 4E3 MAB was generated, i.e., against native protein, while C219 was raised against fully denatured protein.

Figure 3A:
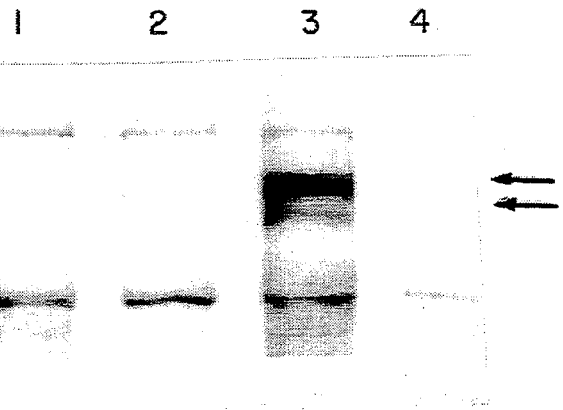
FIG. 3B represents the results of Western blotting of the immunoprecipitated protein of FIG. 3A with the C219 monoclonal antibody.
Figure 3B:
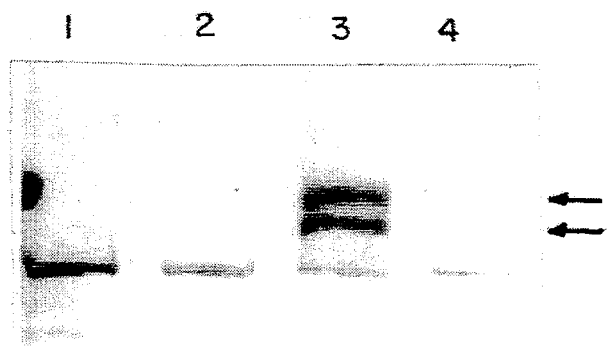

The identity of the protein species immunoprecipitated with 4E3 as mdr P-glycoprotein was further confirmed by first immunoprecipitating with 4E3 followed by transfer of the immunoprecipitated proteins to nitrocellulose paper and performing a Western blot analysis using C219. The immunoprecipitate with 4E3 for metabolically labelled drug sensitive CEM and multidrug resistant CEM/VBL 500 cell lines, was fractionated by SDS electrophoresis and transferred to nitrocellulose paper for Western blot analysis using C219. FIG. 3 shows an autoradiograph of the $^{35}$S-methionine labelled 170 kd protein immunoprecipitated with 4E3 from the multidrug resistant cell line and not from the drug sensitive parent cell line. In addition, a control isotype IgG2a antibody did not reveal any specific immunoprecipitatable proteins in either the mdr or drug sensitive cell lines. FIG. 3B shows the result of Western blotting with C219 of the immunoprecipitated proteins in Panel A demonstrating that the 170 kd protein precipitated with 4E3 is recognized by the C219 anti-P-glycoprotein monoclonal antibody. Western blotting with an isotype specific IgG2a antibody does not detect the proteins precipitated with 4E3.

Figure 4:
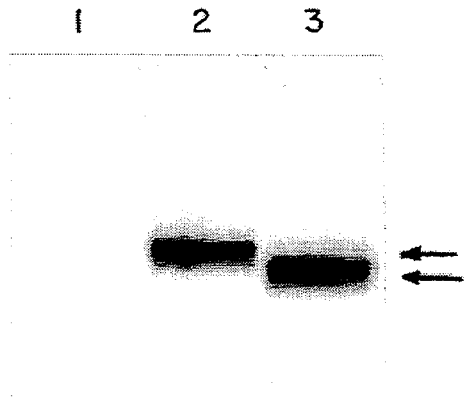
FIG. 4 is an autoradiograph showing immunoprecipitation of nonglycosylated (Lane 3) and glycosylated (Lane 2) forms of P-glycoprotein with MAB 4E3. Lane 1 is a control lane with IgG2a used as an isotype control.

The electrophoretic separation shown in FIG. 3 resolves a doublet both immunoprecipitated by 4E3 and recognized by C219. This doublet most probably represents the fully glycosylated and non-glycosylated forms of P-glycoprotein as no chase with unlabelled methionine was included prior to harvesting the cells for immunoprecipitation. To directly address this issue, we performed immunoprecipitations of metabolically labelled proteins from mdr cells treated with tunicamycin to block N-linked glycosylation. FIG. 4 demonstrates that 4E3 effectively precipitates both non-glycosylated (lane 3) and glycosylated forms of P-glycoprotein (land 2).

Immunohistochemistry using MAB 4E3.

FIG. 5 demonstrates that following fixation of cells in 1% paraformaldehyde, 4E3 is able to specifically stain multidrug resistant cells expressing the P-glycoprotein but does not react to the drug sensitive, non-P-glycoprotein expressing cells. 4E3 is able to specifically stain the SW-1573/500 (FIG. 5A) and Alexander Aria/0.5 (FIG. 5E) multidrug resistant cell lines overexpressing the P-glycoprotein but does not react to the corresponding drug-sensitive parental cell lines (FIGS. 5C and 5G, respectively). Because these cells were fixed with paraformaldehyde, the histochemical signal observed with 4E3 is due to surface staining and not to cytoplasmic P-glycoprotein. Isotype control antibody staining does not react with either the MDR or the parental cell lines (FIGS. 5B, F, D and H, respectively). We have also been able to stain multidrug resistant cells with 4E3 following fixation with brief exposures (1 to 5 minutes at room temperature) to acetone or methanol.

The antibody is also able to detect P-glycoprotein along bile caniliculi in frozen sections of human liver.

MAB 4E3 does not effect intracellular drug accumulation in mdr cells

The intracellular accumulation of $^3$H-Daunomycin and $^3$H-vinblastine in multidrug resistant cells in the presence of different concentrations of 4E3 was compared. These results were compared to the changes observed using verapamil, a known mdr reversal agent. FIG. 6 shows that when 4E3 is bound to mdr cells followed by incubation with $^3$H-Daunomycin (FIG. 6A) or $^3$H-vinblastine (FIG. 6B), no significant increase in intracellular drug accumulation was observed when compared to IgG2A controls. In contrast, verapamil consistently resulted in an approximately 5-fold increase in the intracellular concentration of Daunomycin. The results were not dependent upon the temperature at which 4E3 was allowed to bind to the cells. These data demonstrate that 4E3 does not appear to effect the transport of these cytotoxic agents by P-glycoprotein as does the mdr inhibitor verapamil.

4E3 does not potentiate the cytotoxicity of Daunomycin in mdr cells

The effect of 4E3 on cell growth and survival in the presence of cytotoxic agents was tested. FIG. 7 demonstrates that the presence of 4E3 during incubation of mdr cells with increasing concentrations of Daunomycin does not potentiate the cytotoxicity of Daunomycin. This is true at concentrations of 4E3 as high as 20 $\mu$g/ml. In addition, no effect was observed on the drug sensitive parent cell line. These results are consistent with the lack of effect observed on the intracellular accumulation of Daunomycin in mdr cells (see, FIG. 7).

4E3 is able to detect P-glycoprotein on human leukemic blasts

The ability of 4E3 in determining P-glycoprotein expression in human leukemia specimens was next tested. FIG. 8 show the flow cytometric analysis of two human acute myelogenous leukemia specimens. These results demonstrate that 4E3 is capable of recognizing P-glycoprotein in human leukemia specimens as well as in multidrug resistant cell lines selected in vitro and thus provides a useful reagent for the detection of P-glycoprotein in human leukemia.

MAB 4E3 is able to detect P-glycoprotein on non-malignant bone marrow progenitors The expression of P-glycoprotein in a small percentage of cells in the normal bone marrow has been documented in several reports. More recently, P-glycoprotein expression has been shown to be expressed on a population (less than 5% of the total bone marrow cells) of putative bone marrow stem cells co-expressing the CD34 antigen. During an analysis of patients bone marrow specimens for P-glycoprotein expression using 4E3, we found the surprising result of an extremely high level of P-glycoprotein expression in several specimens which were in the early phases of recovery from chemotherapeutic myelosuppression. Bone marrow cells were obtained from a patient 10 days after receiving myelosuppressive therapy for acute lymphoblastic leukemia. At the time this bone marrow specimen was taken, the patient's peripheral blood counts showed an absolute neutropenia and the bone marrow biopsy showed extreme hypocellularity but not evidence for leukemia. Enough cells were available for only single antibody staining using 4E3. FIG. 9 demonstrate that a majority of the bone marrow cells expressed a very high level of P-glycoprotein. One week later, another bone marrow specimen was obtained which showed a remission bone marrow with less than 5% blasts. Flow cytometric analysis of the cells from this specimen showed a dramatically reduced expression of P-glycoprotein (FIGS. 9B). These results demonstrate that the antibody of the present invention can be used to monitor the expression of P-glycoprotein in human bone marrow, which can be modulated by as yet unknown mechanisms, but appears to be in some manner related to the physiology of bone marrow recovery. Thus, strategies for therapy can be evaluated based upon P-glycoprotein level.

It is evident that those skilled in the art given the benefit of the foregoing disclosure may make numerous modifications thereof and departures from the specific embodiments described herein, without departing from the inventive concepts and the present invention is to be limited solely by the scope and spirit of the appended claims.

We claim:

1. The monoclonal antibody 4E3.
2. An fragment of the antibody of claim 1 which retains the specific binding characteristics of the antibody.
3. A monoclonal antibody which specifically binds the same epitope as monoclonal antibody 4E3 without increasing the intracellular accumulation of DAUNOMYCIN or VINBLASTINE as measured by using 10 to 100 $\mu$g/ml of said antibody per cell when said cell is exposed to 0,001 to 10 $\mu$/ml of DAUNOMYCIN, or 0.1 to 10 $\mu$g/ml of VINBLASTINE, and wherein said antibody does not inhibit the growth of MDR cells as measured by adding up to 20 $\mu$g/ml of the antibody to said MDR cells.
4. An assay for detecting or quantifying the presence of a P-glycoprotein encoded by mdr1 in biological fluid or cells of a human which comprises
   (a) reacting the biological fluid or cell with the antibody of claim 3, and
   (b) determining whether or not binding has occurred.
5. The method of claim 4, where the amount of binding that occurs is quantified.
6. The assay of claim 4, wherein the antibody is labelled with a radionuclide and injected into the human, and determining whether binding occurs is done by detecting the differential accumulation of the radionuclide in the human.
7. The assay of claim 6, wherein a high level of binding is indicative of a tumor cell.
8. The assay of claim 7, wherein the tumor cell is selected from the group consisting of pediatric rhabdomyosarcoma, myeloma neuroblasts, acute myelogenous leukemia, colon carcinoma and adrenocortical carcinoma.
9. The assay of claim 4, wherein the biological fluid or the cell is removed from the human before the antibody is added.
10. The assay of claim 9, wherein the determination of whether binding occurred is by ELISA.
11. A method of monitoring a therapeutic regime in a patient having a tumor which comprises
    (a) reacting the antibody of claim 3 with a bodily fluid or tissue sample of the patient, and
    (b) determining the amount of binding that occurs, and
    (c) comparing the amount of binding to a baseline level.
12. The method of claim 11, wherein the antibody is labelled with a radionuclide and injected into the patient, and determining whether binding occurs is done by detecting the differential accumulation of the radionuclide in the patient.
13. The assay of claim 11, wherein the biological fluid or the cell is removed from the patient before the antibody is added.
14. The assay of claim 13, wherein the determination of whether binding occurred is by ELISA.
15. An fragment of the antibody of claim 3 which retains the specific binding characteristics of the antibody.

16. A hybridoma cell line producing the antibody of claim 3.

17. An assay for quantifying a test compound's effect on the level of P-glycoprotein expression which comprises:
   (a) reacting the antibody of claim 3 with a sample of cells;
   (b) determining the amount of binding that occurs;
   (c) adding the test compound to another sample of the same cells;
   (d) reacting the antibody of claim 24 with the sample of step (c); and
   (e) determining the change in the level of antibody binding compared with step (b).

18. A method of isolating live cells expressing P-glycoprotein without inhibiting the functional transport characteristics of the P-glycoprotein which comprises
   (a) injecting a detectable amount of the antibody of claim 3 conjugated to a detectable label;
   (b) monitoring for binding of the antibody; and
   (c) isolating cells where binding has occurred.

19. The method of claim 18, wherein the detectable label is a radionuclide.

20. The method of claim 19, wherein the monitoring is by use of a scintegraphic camera.

21. A hybridoma cell line having ATCC Accession Number HB11018.

* * * * *